Figure 1:
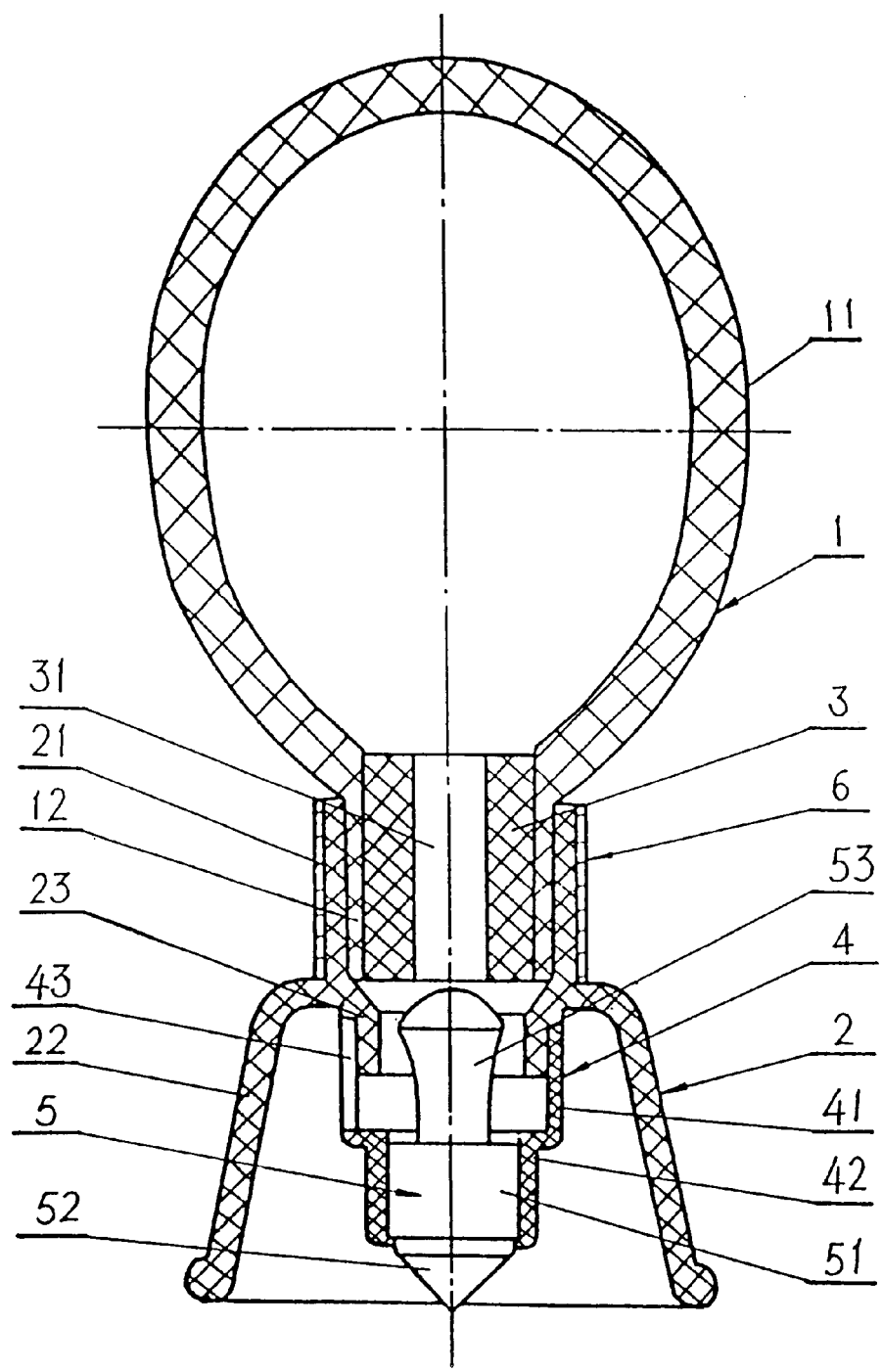

United States Patent

Guo

[11] Patent Number: 5,904,700
[45] Date of Patent: May 18, 1999

[54] MAGNETIC ACUPUNCTURE POINTER

[76] Inventor: Liwen Guo, No. 169 Tongxiang St., Dongli District, Harbin, China

[21] Appl. No.: 08/978,596

[22] Filed: Nov. 26, 1997

[30] Foreign Application Priority Data

Nov. 29, 1996 [CN] China ................................ 96120798

[51] Int. Cl.$^6$ .................................................. A61B 17/34
[52] U.S. Cl. .......................................... 606/189; 606/204
[58] Field of Search .................................. 606/189, 204, 606/185, 186, 188; 600/15

[56] References Cited

U.S. PATENT DOCUMENTS

| | | | |
|---|---|---|---|
| 5,720,046 | 2/1998 | Lopez et al. | 606/204 |
| 5,782,858 | 7/1998 | Cheng | 606/204 |
| 5,792,171 | 8/1998 | Burdenko et al. | 606/189 |
| 5,803,896 | 9/1998 | Chen | 600/9 |

*Primary Examiner*—Michael Buiz
*Assistant Examiner*—Vy Quang Bui
*Attorney, Agent, or Firm*—Antonelli, Terry, Stout & Kraus, LLP

[57] ABSTRACT

The present invention relates to a magnetic apparatus pointer of traditional Chinese medicine for health care, and in particular, relates to a magnetic medicine instrument of acupuncture. The apparatus of pointer includes an air bag, and a permanent magnetic head provided within the hollow case. To operate the pointer of the present invention, the air bag shall be pressed, and at the same time, the hollow case shall be attached closely to the acupuncture point of human body. When the press is released, the air bag restores to the original shape and the air within the hollow case is sucked into said bag, so as to make the magnet head closely attached to the acupuncture point of human body. The pointers with N pole and S pole may be positioned on both sides of human body making vertical cutting lines of magnetic force acting upon human body.

13 Claims, 1 Drawing Sheet

MAGNETIC ACUPUNCTURE POINTER

TECHNICAL FIELD OF THE INVENTION

The present invention relates to an apparatus of traditional Chinese medicine for health care, and in particular, relates to a magnetic medical instrument of acupuncture.

BACKGROUND OF THE INVENTION

In the field of acupuncture of Chinese medicine, the application of magnetic treatment to an acupuncture point of human body is a new physical therapy. In clinical practice of magnetic acupuncture, a main acupuncture point or a plurality of acupuncture points shall be first picked up from human main and collateral channels which relate to the disease, and then a doctor or patient himself fixes the magnetic pole of the magnetic medical instrument to the acupuncture points to be treated. At present, the magnetic medical instruments mainly include magnetic medical instrument, magnets of slice or block shapes and magnetic needle etc.

The present magnetic medical instruments of acupuncture have four defects: firstly, an ordinary magnetic medical instrument may only apply treatment to one or two acupuncture points simultaneously as the number of the magnetic heads is limited, and when such treatment shall be applied to plural points at inner or outer joints of human body or the points requiring bigger magnetic field, the present magnetic medical instrument may not come up to the requirement; secondly, the magnetic poles of the present magnetic medical instrument may not be easily fixed to the acupuncture points to be treated; thirdly, the magnetic heads of the present magnetic medical instrument are of all N poles, which may not form a closed magnetic circuit of N and S poles at the points to be treated and can not achieve better magnetic medical effect, and fourthly, the present magnetic medical instrument has a complicated structure, which results in high price.

Magnets of slice or block shapes may not concentrate the magnetic energy to the points to be treated, and consequently the stimulation of magnetic poles to the points to be treated is weakened. In addition the magnets of slice or block shapes may not easily fixed to the points to be treated.

The application of treatment of magnetic needle may bring pain to patients and in particular it may not be easily operated by the patients themselves.

OBJECTIVE OF THE INVENTION

One objective of the present invention is to provide a magnetic acupuncture pointer of Chinese medicine which may have its magnetic head easily fixed.

Another objective of the present invention is to provide magnetic acupuncture pointer which may form a magnetic field around the points of human body to be treated by placing magnetic heads of N and S around the two sides of acupuncture points (such as inner or outer joints) of human body so as to apply the vertical cutting lines of magnetic force to the human body.

SUMMARY OF THE INVENTION

The magnetic acupuncture pointer according to the present invention includes an air bag, a hollow case having one end open and the other connected to said air bag, and a permanent manager provided within the hollow case.

Said hollow case includes an upper case portion fixed and connected with the outlet opening of said air bag, a lower case portion having therein a connection portion, and a connection portion which is of a hollow column connected with the base of the permanent magnet. Said base of the permanent magnet includes an upper transitional portion being connected and fixed with said connection portion of said hollow case and having a through hole on the said wall, and a lower base fixed therein with a permanent magnet. Said permanent magnet includes permanent magnetic block and magnetic head. The top of said permanent magnet has a magnetic yoke, and said permanent magnetic block has a magnetic head being made of metal materials with good magnetic conductivity and forming a close magnetic circuit with said permanent magnet. For example, said magnetic head may be made of pure iron low-carbon steel so as to lengthen the magnetic lines of force. Said magnetic head is of N pole or S pole. Each set of magnetic acupuncture pointer may have one or more single pointers of N pole or of S pole. The outlet of said air bag may be provided with a hollow supporting column preventing the adhesive binding at the outlet of said air bag. Said magnetic head may be in the shape of cone, sphere or plate, depending upon the needs of different acupuncture points. The outer surface of said magnetic head may be gold or silver coated for rust prevention and sterilization. In order to prevent confusion among the single acupuncture pointers with different magnetic poles, the outer surface of said permanent magnet base, air bag or hollow case may be painted with different colors distinguishing magnetic poles of said magnetic pointer, a fastening ring may be provided to the outer said supporting column, outlet of air bag and said upper portion of said hollow case so that they may be pressingly fixed together. Said hollow case may be made of transparent materials such as organic glass and the air bag may be made of rubber, plastic, soft plastic or metal materials.

Compared with the prior art, the present invention is simple in structure and easy in fixing magnetic head. A set of magnetic pointer may comprise a pair of or even several tens of pairs of single magnetic acupuncture pointers with N and S poles, which may be used by pairs, and when positioned on two sides of human body, they may form a relevant magnetic field so as to let vertical cutting lines of magnetic force acting upon human body. The acupuncture pointers may be attached, under the negative air pressure, to various points of human body and the silver needle tips of said magnetic heads may pressingly point the acupuncture points under the negative air pressure.

Preferred Embodiment

Embodiment of the present invention may be detailed by reference to the following drawings.

FIG. 1 is a sectional view of structure of present invention.

The magnetic pointer as shown by FIG. 1 includes an air bag 1, a hollow case 2, a supporting column 3, a permanent magnet base 4, permanent magnet 5 and fastening ring 6.

The upper part of the air bag 1 is bag body 11, and the lower extension part is the outlet 12 which has the outer surface connected with the upper case portion 21 of the hollow case.

Said hollow case has an upper case portion 21, a lower case portion 22 and a connection portion 23. The connection part of said upper portion 21 and said lower portion 22 extends downward outside of said connection portion 23, and the outer surface of said connection portion 23 is connected and fixed with said permanent magnetic base 4.

The supporting column 3 may support the outer 12 of said air bag 1. Supporting column 3 is of barrel shape, provided within said outer 12 wherein a cavity 31 is the inhaling and expelling passage of said air bag.

The permanent magnetic base 4 includes a transitional portion 41 and base 42, wherein said portion 41 has its inner wall housed joint with said connection portion 23. One side of said transitional portion 41 of said permanent magnet base 4 has an air hole 43. A permanent magnet 5 is fixed within a base body 42 of said permanent magnet base 4. The outer surface of said permanent magnet base 4 is painted with color to distinguish the polarization of the magnet head 52. For example, when N pole of said permanent magnet faces outside, i.e. magnet head 52 is of N pole, the outer surface of said base 4 is painted with blue color; similarly, when head 52 is of S pole, the outer surface of said base 4 is painted with red color.

The permanent magnet 5, fixed within the base 4, has a permanent magnet block 51 and magnet head 52. On the top of said block 51 there is provided with a magnetic yoke 53, and said permanent magnet block 51 has its bottom attached with a magnet head 52 made of metal materials with good magnetic conductivity. Said head 52 may be made with pure iron or low-carbon steel, lengthening the magnetic line by 10~20 mm. The head 52 in the present embodiment is cone shaped, and according to the different acupuncture pints, the head 52 may be of sphere or plate. The head 52 and the block 51 form a close magnet circuit. The outer surface of the head 52 and the block 51 form a close magnet circuit. The outer surface of the head 52 is silver or gold-coated.

The fastening ring 6 joints in turn, from inner side to the outer, said supporting column 3, outlet 12 of the air bag 1, and said upper case portion 21 of said hollow case 2 together.

One set of magnetic pointer includes two sets of single pointers, head 52 of one set having N pole while the other set having S pole, and each set comprising 1 to 36 single magnetic acupuncture pointers.

The air bag 1 of the present embodiment may be made of rubber, soft plastic. The hollow case 2, supporting column 3, permanent magnet base 4 and fastening ring 6 may be made of rubber, plastic or metal materials, and said hollow case 2 may also be made of transparent plastic or organic glass so as to inspect from outside the application and medical treatment.

To operate the pointer of the present invention bag body 11 of said air bag 1 shall be pressed, and at the same time, case 2 shall be attached closely to the acupuncture point of human body. When the press is released, the body 11 restores to the original shape and the air within the case 2 is sucked into said bag 1 through said air hole 43 making negative pressure, so as to make it fixingly attached to the acupuncture points of human body. The pointers with N pole and S pole may be positioned on both sides of human body making vertical cutting lines of magnetic force acting upon human body. The silver tip of said head 52 pressingly points the acupuncture point under the negative pressure, applying magnetic treatment to the acupuncture point of human body thus achieving better magnetic medicine effects.

The above is only a better mode of embodiment of present invention and is not limited thereto. Any simple variation, alteration or change to the above embodiment based on the technical substance of the present invention shall fall within the scope of the technical solution of the present invention.

What is claimed:

1. A magnetic acupuncture pointer, including an air bag, a hollow case and a permanent magnet, wherein said hollow case has one end open and the other end connected with said air bag, and said permanent magnet is provided within said hollow case.

2. A magnetic acupuncture pointer according to claim 1, wherein said hollow case includes an upper case portion connected and fixed with an outlet of said air bag, a lower case portion having a connecting portion, and a connection portion, said connection portion is a hollow column and is fixed to a permanent magnet base.

3. A magnetic acupuncture pointer according to claim 2, wherein said permanent magnet base includes a upper transitional portion and a lower base, and said transitional portion is connected and fixed with said connection portion of said hollow case and has on its side wall a hole, and a permanent magnet is provided within said base.

4. A magnetic acupuncture pointer according to claim 3, wherein said permanent magnet includes a permanent magnetic block and a magnetic head, on the top of said permanent magnet there is provided with a magnetic yoke, and said permanent magnet is fixed with the magnetic head forming a close magnetic circuit with said magnetic block.

5. A magnetic acupuncture pointer according to claim 4, wherein magnetic head has a N pole.

6. A magnetic acupuncture pointer according to claim 4, wherein magnetic head has a S pole.

7. A magnetic acupuncture pointer according to claim 4, wherein said outlet of said air bag has a hollow supporting column.

8. A magnetic acupuncture pointer according to claim 7, wherein said magnetic head has a shape of cone, sphere or plate.

9. A magnetic acupuncture pointer according to claim 8, wherein the surface of said magnetic head has a layer of gold or silver coating for rust prevention or sterilization.

10. A magnetic acupuncture pointer according to claim 9, wherein the outer surface of said permanent magnet is painted with different colors for distinguishing magnetic poles of magnetic heads.

11. A magnetic acupuncture pointer according to claim 9, wherein the outer surface of said hollow case is painted with different colors for distinguishing magnetic poles of magnetic heads.

12. A magnetic acupuncture pointer according to claim 4, wherein there is provided with a fastening ring housed the outside of said supporting column, outlet of said air bag and said upper portion of said hollow case, pressingly joining said supporting column, outlet of said air bag and said upper portion of said hollow case.

13. A magnetic acupuncture pointer according to claim 12, wherein said hollow case is made of transparent materials.

* * * * *